US012667548B2

(12) United States Patent
Kern et al.

(10) Patent No.: US 12,667,548 B2
(45) Date of Patent: Jun. 30, 2026

(54) TREATMENT OF RETINITIS PIGMENTOSA AND RETINITIS PIGMENTOSA ASSOCIATED WITH USHER SYNDROME WITH N-ACETYLCYSTEINE AMIDE

(71) Applicant: Nacuity Pharmaceuticals, Inc., Fort Worth, TX (US)

(72) Inventors: Jami Kern, Fort Worth, TX (US); G. Michael Wall, Fort Worth, TX (US)

(73) Assignee: Nacuity Pharmaceuticals, Inc., Fort Worth, TX (US)

( * ) Notice: Subject to any disclaimer, the term of this patent is extended or adjusted under 35 U.S.C. 154(b) by 0 days.

(21) Appl. No.: 19/338,634

(22) Filed: Sep. 24, 2025

(65) Prior Publication Data

US 2026/0014102 A1 Jan. 15, 2026

Related U.S. Application Data

(63) Continuation-in-part of application No. 15/523,665, filed as application No. PCT/US2015/059589 on Nov. 6, 2015, now Pat. No. 12,472,157.

(60) Provisional application No. 62/076,594, filed on Nov. 7, 2014.

(51) Int. Cl.
*A61K 31/16* (2006.01)
*A61P 27/02* (2006.01)

(52) U.S. Cl.
CPC .............. *A61K 31/16* (2013.01); *A61P 27/02* (2018.01)

(58) Field of Classification Search
CPC ................................ A61K 31/16; A61P 27/02
See application file for complete search history.

(56) References Cited

U.S. PATENT DOCUMENTS

| | | | |
|---|---|---|---|
| 1,114,369 | A | 10/1914 | Kukla |
| 3,340,147 | A | 9/1967 | Alexander |
| 5,874,468 | A | 2/1999 | Atlas |
| 6,420,429 | B1 | 7/2002 | Atlas |
| 8,354,449 | B2 | 1/2013 | Goldstein |
| 8,937,099 | B2 | 1/2015 | Goldstein |
| 8,993,627 | B2 | 3/2015 | Goldstein |
| 9,216,162 | B2 | 12/2015 | Goldstein |
| 9,763,902 | B2 | 9/2017 | Warner |
| 9,889,103 | B2 | 2/2018 | Warner |
| 10,869,846 | B2 | 12/2020 | Goldstein |
| 11,052,018 | B2 | 7/2021 | Molnar |
| 11,092,017 | B2 | 8/2021 | Propheter-Hinckley |
| 2003/0027745 | A1 | 2/2003 | Repine |
| 2005/0112572 | A1 | 5/2005 | Pincemail |
| 2009/0234011 | A1 | 9/2009 | Goldstein |
| 2012/0142550 | A1 | 6/2012 | Zehnder |
| 2012/0150029 | A1 | 6/2012 | Debuc |
| 2013/0303436 | A1 | 11/2013 | Wilson |
| 2015/0164830 | A1 | 6/2015 | Goldstein |
| 2017/0020914 | A1 | 1/2017 | Castro Feo |
| 2017/0333375 | A1 | 11/2017 | Campochiaro |
| 2017/0370945 | A1 | 12/2017 | Campochiaro |
| 2019/0135741 | A1 | 5/2019 | Wall |
| 2020/0281944 | A1 | 9/2020 | Piraee |
| 2021/0228509 | A1 | 7/2021 | Wall |
| 2026/0083688 | A1* | 3/2026 | Wall ....................... A61K 31/16 |

FOREIGN PATENT DOCUMENTS

| | | | |
|---|---|---|---|
| CA | 3078680 | A1 | 5/2019 |
| CA | 3079196 | C | 5/2021 |
| CN | 108618993 | A | 10/2018 |
| EP | 1975621 | A4 | 2/2009 |
| GB | 1114369 | A | 5/1968 |
| JP | 2005350405 | A | 12/2005 |
| JP | 2008538586 | A5 | 7/2009 |
| JP | 2013533234 | A | 8/2013 |
| JP | 202023549 | | 2/2020 |
| WO | 2003016527 | A3 | 12/2003 |
| WO | 2004012652 | A3 | 4/2004 |
| WO | 2004028536 | A1 | 4/2004 |
| WO | 2006116353 | A2 | 11/2006 |
| WO | 2010048716 | A1 | 5/2010 |
| WO | 2011044230 | A2 | 4/2011 |
| WO | 2013138744 | A1 | 9/2013 |
| WO | 2013163545 | A1 | 10/2013 |
| WO | 2014025792 | A1 | 2/2014 |
| WO | 2014100361 | A1 | 6/2014 |
| WO | 2015148880 | A1 | 10/2015 |
| WO | 2016073931 | A1 | 5/2016 |
| WO | 2016073829 | A9 | 6/2016 |
| WO | 2017161318 | A1 | 9/2017 |
| WO | 2019060623 | A1 | 3/2019 |
| WO | 2019060634 | A1 | 3/2019 |
| WO | 2019060704 | A1 | 3/2019 |
| WO | 2019094383 | A1 | 5/2019 |
| WO | 2019097434 | A1 | 5/2019 |

(Continued)

OTHER PUBLICATIONS

Birch et al.; JAMA Ophthalmol.; Sep. 2013; 131(9): pp. 1143-1150.*

Nacuity Press Release "Nacuity Pharmaceuticals Announces Positive Data from Clinical Trial Evaluating NPI-001 to Treat Retinitis Pigmentosa Associated with Usher Syndrome"; published Sep. 11, 2025.*

Komeina, et al., "Blockade of neuronal nitric oxide synthase reduces cone cell death in a model of retinitis pigmentosa." Free Radic Biol Med, (2008), 45(6):905-12.

Kunisada, et al. "CXCL1 Inhibition Regulates UVB-Induced Skin Inflammation and Tumorigenesis in Xpa-Deficient Mice" Journal of Investigative Dermatology (2017), 137, 1975-1983.

Kusmierek, et al., Ultraviolet derivatization of low-molecular-mass thiols for high performance liquid chromatography and capillary electrophoresis analysis, J Chrom B, 879 (2011) 1290-1307.

(Continued)

*Primary Examiner* — Jeffrey T. Palenik

(74) *Attorney, Agent, or Firm* — Edwin S. Flores; Daniel J. Chalker; Chalker Flores, LLP

(57) ABSTRACT

Provided herein are methods for the treatment of retinitis pigmentosa in a human that comprises administering to the human a therapeutically effective amount of N-acetylcysteine amide (NACA).

20 Claims, 5 Drawing Sheets

(56) References Cited

FOREIGN PATENT DOCUMENTS

| | | | |
|---|---|---|---|
| WO | 2019103915 | A1 | 5/2019 |
| WO | 2020102810 | A1 | 5/2020 |
| WO | 2020146660 | A1 | 7/2020 |
| WO | 2020146666 | A1 | 7/2020 |
| WO | 2020146674 | A1 | 7/2020 |

OTHER PUBLICATIONS

Grinberg, et al., "N-acetylcysteine amide, a novel cell-permeating thiol, restores cellular glutathione and protects human red blood cells from oxidative stress," Free Radical Biol Med. (2005) ;38(1):136-145.
Lee, et al., "N-Acetylcysteine Promotes Long-Term Survival of Cones in a Model of Retinitis Pigmentosa," J Cell Physiol (2011), 226:1843-1849, published online Nov. 10, 2010.
Levine, R.L., "Carbonyl modified proteins in cellular regulation, aging, and disease" Free Radic Biol Med, 2002. 32(9): p. 790-6.
Li, et al., "A Convenient Synthesis of Amino Acid Methyl Esters", Molecules (2008), 13:1111-1119.
Liu, et al., "A rabbit model to study biochemical damage to the lens after vitrectomy: effects of N-acetylcysteine." Exp Eye Res. 2009;88(6):1165-70.
Lu, et al., "Effects of Different Types of Oxidative Stress in RPE Cells," J Cell Phys (2006), 206(1):119-125.
Maddirala, et al. "Prevention and reversal of selenite-induced cataracts by N-acetylcysteine amide in Wistar rats" BMC Ophthalmology (2017) 17:54.
Maeda, et al., "Important Role of the 3-Mercaptopropionamide Moiety in Glutathione: Promoting Effect on Decomposition of the Adduct of Glutathione with the Oxoammonium Ion of TEMPO", J Organic Chem (2005). 70:8338-8343.
Martin, Tellis, "Amides of N-Acylcysteines as Mucolytic Agents", J Med Chem (1967), 10:1172-1176.
Martinez-Fernandez De La Camara, et al., Altered Antioxidant-Oxidant Status in Aqueous Humor and Peripheral Blood of Patents with Retinitis Pigmentosa, PLOS One (2013), 8(9):E74223.
McMenamim, et al., Simultaneous analysis of multiple aminothiols in human plasma by high performance liquid chromatography with fluorescence detection, J Chrom B, 877 (2009) 3274-3281.
Minozzi, et al., "An Insight into the Radical Thiol/Yne Coupling: The Emergence of Arylalkyne-tagged Suggars for te Direct Photoinduced Glycosylation of Cysteine Containing Peptides", J. Org. Chem, 2011, 76, 450-459.
Miller, WF. "Aerosol therapy in acute and chronic respiratory disease." Arch Intern Med 1973;131:148-155.
Monostori, et al., Determination of glutathione and glutathione disulfide in biological samples: an in-depth review. J Chrom B, 877 (2009) 3331-3346.
Moore, et al., A new LC-MS/MS method for the clinical determination of reduced and oxidized glutathione from whole blood. J Chrom B, 929 (2013) 51-55.
Nakagami, et al. "A novel Nrf2 activator from microbial transformation inhibits radiation-induced dermatitis in mice," Journal of Radiation Research, vol. 57, No. 5, 2016, pp. 567-571.
Nash, et al., "Nebulized and oral thiol derivatives for pulmonary disease in cystic fibrosis." Cochrane Database Syst Rev 2009;(1):CD007168.
New, et al., Evaluation of BEH C18, BEH HILIC, and HSS T3 (C18) Column Chemistries for the UPLC-MS-MS Analysis of Glutathione, Glutathione Disulfide, and Ophthalmic Acid in Mouse Liver and Human Plasma. J Chrom Sci, 46 (2008) 209-214.
Niemeyer, Selective Rod- and Cone-ERG Responses on Retinal Degenerations, Digital Journal of Ophthalmology, 1998, vol. 4, No. 10, 1998.
Nozal, et al., Determination of glutathione, cysteine, and N-acetylcysteine in rabbit eye tissues using high-performance liquid chromatography and post-column derivatization with 5,5'-dithiobis(2-nitrobenzoic acid). J Chrom A, 778 (1997) 347-353.
Offen, et al. "A low molecular weight copper chelator crosses the blood-brain barrier and attentuates experimental autoimmune encephalomyelitis" Journal of Neurochemistry, 2004, 89, 1241-1251.
Park, et al.: "Targeted and Reversible Blood-Retinal Barrier Disruption via Focused Ultrasound and Microbubbles" PLoS One (2012), 7(8):e42754.
Poole, et al., "Mucolytic agents versus placebo for chronic bronchitis or chronic obstructive pulmonary disease." Cochrane Database Syst Rev 2015;(7):CD001287).
Reagan-Shaw, et al. "Dose translation from animal to human studies revised" The FASEB Journal, Mar. 2007, vol. 22, (659-661).
Reyes, et al., Neuronal glutathione content and antioxidant capacity can be normalized in situ by N-acetyl cysteine concentrations attained in human cerebrospinal fluid, Neurotherapeutics, 13 (2016) 217-225.
Riley, et al., "Glutathione in the aqueous humor of human and other species." Investigative ophthalmology & visual science, (1980), 9(1):94-96.
Rubin BK. "Aerosol Medications for Treatment of Mucus Clearance Disorders Respiratory care" 2015; 60(6): 825-832.
Šalamon, et al., "Medical and Dietary Uses of N-Acetylcysteine." Antioxidants 2019, 8, 111.
Schimel, et al., "N-Acetylcysteine Amide (NACA) Prevents Retinal Degeneration by Up-Regulating Reduced Glutathione Production and Reversing Lipid Peroxidation." The American Journal of Pathology, (2011), 178 (5):2032-2043.
Sekhon, "Exploiting the Poer of Stereochemistry in Drugs . . . ", Journal of Modern Medicinal Chemistry, 2013, 10-36.
Shams, et al. "Treatment of corneal cystine crystal accumulation in patients with cystinosis" Clinical Opthamalogy, Oct. 10, 2014, 2077-2078.
Shen, et al., "Oxidative damage is a potential cause of cone cell death in retinitis pigmentosa." J Cell Physiol, (2005), 203(3):457-64.
Shen, et al., "Oxidative damage in age-related macular degeneration," Histology and Histopathology (2007), 22 (12):1301-1308.
Shintani, et al., "Review and Update: Current treatment trends for Patients with Retinitis Pigmentosa," Optometry (2009), 80:384-401.
Sunitha, et al. "N-Acetylcysteine amide: a derivative to fulfill the promises of N-Aceylcysteine" Free Radical Resarch, May 2013, 47(5), 357-367.
Supelco "Methanolic H2S04 (10./o v/v)" 1997, Sigma-Aldrich Co., 2 Pages.
Squellerio, et al., Direct glutathione quantification in human blood by LC-MS/MS: comparison with HPLC with electrochemical detection. J Pharm Biomed Anal, 71 (2012) 111-8.
Stey, et al., "The effect of oral N-acetylcysteine in chronic bronchitis: a quantitative systematic review." Eur Respir J. 2000; 16(2):253-62.
Suh, et al., Clinical assay of four thiol amino acid redox couples by LC-MS/MS: utility in thalassemia, J Chrom B, 877 (2009) 3418-3427.
Sunitha, et al., N-acetylcysteine amide: a derivative to fulfull the promises of N-acetylcysteine. Free Radic Res, 47 (2013) 357-367.
Tam, et al., "Nebulized and oral thiol derivatives for pulmonary disease in cystic fibrosis." Cochrane Database Syst Rev 2013;(7):CD007168.
Tarrant et al. "Mucoactive agents for adults with acute lung conditions: A systematic review." Heart & Lung (2019) 48 (2):141-147.
Tobwala et al. "N-acetylcysteine Amide (NACA), a Novel GSH Prodrug: Its Metabolism and Implications in Health", Labrou, 2013, Capter VI. ISBN:978-1-62417-460-5.
Tsai, et al. "Topical TV-Acetylcysteine Accelerates Wound Healing in Vitro and in Vivo via the PKC/Stat3 Pathway" Int. J. Mol. Sci., 2014, 15, 7563-7578.
Tse, et al., "High-dose N-acetylcysteinine in stable COPD: the 1-year, double-blind, randomized, placebo-controlled HIACE study." Chest, (2013). 144(1):106-118.
Tuson, et al., "Overexpression of CERKL, a gene responsible for retinitis pigmentosa in humans, protects cells from apoptosis induced by oxidative stress." Mol Vis. (2009), 15:168-80.

(56) References Cited

OTHER PUBLICATIONS

University of Sao Paulo, et al. "N-Acetyl Cysteine for Cystinosis Patients", ClinicalTrials.gov [online], identifier: NCT01614431, Last update posted: Jun. 20, 2012, https://clinicaltrials.gov/ct2/show/NCT01614431, [retrieved online Jul. 9, 2021].
Adil, et al. "N-acetylcysteine in dermatology" Indian Journal of Dermatology, Feb. 2018.
Amer, et al., "N-acetylcysteine amide (AD4) attenuates oxidative stress in beta-thalassemia blood cells." Biochimica et Biophysica Acta 1780 (2008) 249-255.
Ates, et al., "Antioxidant and free radical scavenging properties of N-acetylcysteine amide (NACA) and comparison with N-acetylcysteine (NAC)." Free Radic Res. (2008), 42(4):372-7.
Babizhayev, et al., Revival of the Lens Transparency with N-Acetylcarnosine.: Current Drug Therapy, 2006:1; 91-116.
Bahat-Stroomza, et al., A novel thiol antioxidant that crosses the blood brain barrier protects dopaminergic neurons in experimental models of Parkinson's disease. European Journal of Neuroscience, 2005; 21: 637-646.
Banerjee, et al., "HIV proteins (gp120 and Tat) and methamphetamine in oxidative stress-induced damage in the brain: Potential role of the thiol antioxidant N-acetylcysteine amide." Free Radic Biol Med. May 15, 2010; 48(10): 1388-1398.
Bean, et al., "Comparative evaluation of antioxidant reactivity within obstructed and control rabbit urinary bladder tissue using FRAP and CUPRAC assays," Molecular and Cellular Biochemistry (2008) 323(1-2):139-142.
Bernardes, et al., "From Disulfide- to Thioether-Linked Glycoproteins" Angewandte Chemie, Supporting Information (2008), S1-S97.
Betteridge, John What is Oxidative Stress Metabolism, vol. 49, No. 2, Feb. 2000, pp. 3-8.
Boone, Kevin "The K-Zone: Biophysical Data Tables", 1994-2006, downloaded from www.kevinboone.com on Mar. 14, 2009.
Buss, et al., "Protein carbonyl measurement by a sensitive ELISA method." Free Radic Biol Med, (1997), 23(3):361-6.
Campochiaro, et al., "Oral N-acetylcysteine improves cone function in retinitis pigmentosa patients in phase I trial." J Clin Invest. 2020 130(3):1527-1541.
Campochiaro, et al. "Is there Excess Oxidative Stress and Damage in Eyes of Patients with Retinitis Pigmentosa" Antioxidants Redox Signaling, (2015) 23(7):643-648.
Campochiaro, et al. "The Mechanism of Cone Cell Death in Retinitis Pigmentosa", Progress in Retinal and Eye Research (2018), 62:24-37.
Carey, et al., "In vivo inhibition of l-buthionine-(S, R)-sulfoximine-induced cataracts by a novel antioxidant, N-acetylcysteine amide." Free Radical Biol Med. 2011;15.
Carey, et al. "N-acetyl-L-cysteine amide protects retinal pigment epithelium against methamphetamine-induced oxidative stress" Journal of Biophysical Chemistry, vol. 3, No. 2, 101-110 (2012).
Carroll, et al., "Simultaneous quantitation of oxidized and reduced glutathione via LC-MS/MS: An insight into the redox state of hematopoietic stem cells." Free Radical Biology and Medicine, 97 (2016) 85-94.
Celma, et al., "Determination of N-acetylcysteine in human plasma by liquid chromatography coupled to tandem mass spectrometry." J Chrom A, 870 (2000) 13-22.
Chastain, et al. "Distribution of topical ocular nepafenac and its active metabolite amfenac to the posterior segment of the eye." Exp Eye Res (2016), 145:58-67.
Cherqui, et al. "The renal Fanconi syndrome in cystinosis: pathogenic insights and therapeutic perspectives" Nal Rev Nephrol. Feb. 2017: 13(2): 115-131.
Clarke, et al. Effect of mucolytic and expectorant drugs on tracheobronchial clearance in chronic bronchitis. Eur J Respir Dis Suppl 1980;110:179-191 (Cant Find).
Davies, et al., "Measurements of protein carbonyls, ortho- and meta-tyrosine and oxidative phosphorylation complex activity in mitochondria from young and old rats." Free Radic Biol Med, (2001), 31(2):181-90.
Demirel, et al. "The preventive effect of N-acetylcysteine on radiation-induced dermatitis in a rat model" Journal of BUON, 15:577-582, 2010.
Devries, et al. "N-acetyl-l-cysteine." J Cell Biochem Suppl (1993), 17F:270-277.
Dietz, et al., "Photochemical Reduction of 5-Bromouracil by Cysteine Derivatives and Coupling of 5-Bromouracil to Cystine Derivatives," Photochemistry and Photobiology (1989), 49(2):121-129.
Dietzsch, et al., "Cystic fibrosis: comparison of two mucolytic drugs for inhalation treatment (acetylcysteine and arginine hydrochloride)." Pediatrics 1975;55:96-100.
Dong, et al., "Compared with N-acetylcysteine (NAC), N-Acetylcysteine Amid (NACA) Provides Increased Protein of Cone Function in a Model of Retinitis Pigmentosa." Investigative Ophthalmology Visual Science, (2014), 55:1-2. (Abstract).
Ehre, et al. An Improved Inhaled Mucolytic to Treat Airway Muco-obstructive Diseases. Am J Respir Crit Care Med. Jan. 15, 2019;199(2):171-180. doi: 10.1164/rccm.201802-0245OC.
Elmonem, et al. "Cystinosis: a review" Orphanet Journal of Rare Diseases (2016) 11:47.
Ercal, et al., "Effects of a thiol antioxidant in various cataract models," Acta Ophthalmologica (2016), 94:S256 (Abstract).
Ercal, et al., High-performance liquid chromatography assay for N-acetylcysteine in biological samples following derivatization with N-(1-pyrenyl)maleimide. J Chrom B, 685 (1996) 329-334.
Eye Health—No. 25, Eye Health, Special Topic: Drug therapy of human eye disease, Planning and production by Soshinsha, Co., Ltd., 2012, p. 1-7, URL https://www.skk-net.com/health/me/files/Eye25_1902_2.pdf.
Frost, et al. "Synthesis of diacylated-glutamyl-cysteamine prodrugs, and in vitro evaluation of their cytotoxicity and intracellular delivery of cysteamine" Eur. J. Med Chem. 109 (2016) 206-215.
Giustarini, et al., Pitfalls in the analysis of the physiological antioxidant glutathione (GSH) and its disulfide (GSSG) in biological samples: an elephant in the room. J Chrom B., 1019 (2016) 21-28.
Han, et al., "Efficacy of nebulized acetylcysteine for relieving symptoms and reducing usage of expectorants in patients with radiation pneumonitis." Thoracic Cancer 2018; 1-6. doi: 10.1111/1759-7714.12938.
Hong, et al. "Effect of High-Dose Intravenous N-acetylcysteine on the Concentration of Plasma Sulfur-Containing Amino Acids", The Korean Journal of Internal Medicine: 20:217-223, 2005.
Heymann, et al., "The preparation and Some Biological Properties of the Asperagine Analog L-2@-Amino-2-carboxyethanesulfonamide," J Am Chem Soc (1959), 81(19):5125-5128.
Hsu, et al. "Feasibility of corneal drug delivery of cysteamine using vitamin E modified silicone hydrogel contact lenses" European Journal of Pharn1aceutics and Biopharn1aceutics 85 (2013) 531-540.
Isokawa, et al., Analytical methods involving separation techniques for determination of low-molecular-weight biothiols in human plasma and blood. J Chrom B, 964 (2014) 103-115.
Israel, et al. Aspirin and N-acetylcysteine co-administration markedly inhibit chronic ethanol intake and block relapse binge drinking: Role of neuroinflammation-oxidative stress self-perpetuation. Addiction Biology. 2019;e12853. (Cant Find).
Jastrzębska, et al., "N-acetylcysteine amide (AD4) reduces cocaine-induced reinstatement." Psychopharmacology 2016;33:3437-3448.
Jones, "Extracellular Redox State: Refining the Definition of Oxidative Stress in Aging," Rejuvenation Research (2006), 9(2):169-181.
Kahns, et al., "Prodrugs as drug delivery systems. 107. Synthesis and chemical and enzymatic hydrolysis kinetics of various mono- and diester prodrug of N-acetylcysteine." Int J Pharm (1990), 62:193-205.
Katz, et al., Cerebrospinal fluid concentrations of N-acetylcysteine after oral administration in Parkinsons disease. Parkinsonism and Related Disorders, 21 (2015) 500-503.
Katz, et al. "Contrast Sensitivity Function in Nephropathic Cystinosis", Arch Ophthalmol vol. 105, 1987).
Kelly, "Clinical applications of N-acetylcysteine." Altern Med Rev J Clin Ther. (1998), 3(2):114-27.

(56) References Cited

OTHER PUBLICATIONS

Kim, et al., "N-Acetylcysteine increases corneal cell survival in a mouse model of Fuchs endothelial corneal dystrophy," Experimental Eye Research (2014), 127:20-25.
Kitamura, Masaki "Drug form and route of the drug" Otolaryngology outlook, vol. 45 (2002) No. 5, Category: 2002 45 vol. 5 No. p. 381-384 (in Japanese).
Komeima, et al., "Antioxidants reduce cone cell death in a model of retinitis pigmentosa." PNAS, (2006), 103 (30):11300-11305.
Komeina, et al., "Antioxidants slow photoreceptor cell death in mouse models of retinitis pigmentosa." J Cell Physiol. (2007), 213(3):809-15.
Usui, et al., "Overexpression of SOD in retina: Need for increase in H202-detoxifying enzyme in same cellular compartment," Free Radical Biology and Medicine (2011 ), 51(7):1347-1354.
Usui, et al., "Increased expression of catalase and superoxide dismutase 2 reduces cone cell death in retinitis pigmentosa." Mol Ther J Am Soc Gene Ther. (2009), 17(5):778-86.
Usui, et al., "NADPH oxidase plays a central role in cone cell death in retinitis pigmentosa." J Neurochem. (2009), 110(3):1028-37.
Vaisbich, et al. "Oxidative Stress in Cystinosis Patients" Nephron Extra, 2011; 1:73-77, publishes online Sep. 19, 2011.
Wang, et al., "Relationship of protein-glutathione mixed disulfide and thioltransferase in H2O2-induced cataract in cultured pig lens." Exp Eye Res. May 1997;64(5):693-700.
Wang, et al., "Hyperoxia-induced lens damage in rabbit: protective effects of N-acetylcysteine." Mol Vis. 2009;15:2945-52.
Watanabe, et al., "Skin-whitening and skin-condition-improving effects of topical oxidized glutathione: a double-blind and placebo-controlled clinical trial." Clin Cosmetic Inv Dermatol. 2014;7:267-274.
Weng, Bioanalytical liquid chromatography tandem mass spectrometry methods on underivatized silica columns with aqueous/organic mobile phases. J Chrom B, 796 (2003) 209-224.
Wu, et al., "Effects of N-acetylcysteine amide (NACA, a thiol antioxidant on radiation-induced cytotoxicity in Chenese hamster ovary cells," Life Sciences (2008), 82:1122-1130.
Wu, et al., Separation and quantification of N-acetyl-L-cysteine and N-acetyl-cysteine-amide by HPLC with fluorescence detection. Biomed Chromatogr, 20 (2006) 415-422.
Yigit, et al. "Release of N-acetylcysteine and N-acetylcysteine Amide from Contact Lenses" Eye Contact Lens, vol. 39, No. 5, Sep. 2013.
Yu, et al., "Intraretinal oxygen levels before and after photoreceptor loss in the RCS rat." Invest Ophthalmol Vis Sci, (2000), 41(12):3999-4006.
Zhang, et al., "Effects of N-acetylcysteine and glutathione ethyl ester drops on streptozotocin-induced diabetic cataract in rats." Mol Vis. 2008;14:862-70.

* cited by examiner

P-values presented are two-sample t-tests to assess change from baseline treatment differences at each visit

TREATMENT OF RETINITIS PIGMENTOSA AND RETINITIS PIGMENTOSA ASSOCIATED WITH USHER SYNDROME WITH N-ACETYLCYSTEINE AMIDE

CROSS-REFERENCE TO RELATED APPLICATIONS

This application is a Continuation-in-Part of U.S. patent application Ser. No. 15/523,665, filed May 1, 2015, and is a U.S. 371 National Phase Application from PCT No. PCT/US2015/059589 international filing date of Nov. 6, 2015, entitled Treatment of Retinitis Pigmentosa with N-Acetylcysteine Amide, and claims benefit of U.S. Provisional U.S. Ser. No. 62/076,594, filed on Nov. 7, 2014, the entire contents of which are incorporated herein by reference.

STATEMENT OF FEDERALLY FUNDED RESEARCH

None.

TECHNICAL FIELD

The present disclosure relates in general to the treatment of retinitis pigmentosa, and more particularly, to the treatment of retinitis pigmentosa.

BACKGROUND

Without limiting the scope of the disclosure, its background is described in connection with Retinitis Pigmentosa (RP), which is a term used for a genetically heterogenous group of inherited retinal degenerations. Findings may be limited to the eyes or the eye findings may be part of a syndrome the most common of which is Usher's Syndrome in which deafness accompanies the retinal disease. In each disorder the inciting event is a mutation that leads to the death of rod photoreceptors, initially causing night blindness. Rods are the major consumers of oxygen in the retina and the loss of rods causes an increase in the tissue oxygen level in the outer retina. This activates NADPH oxidase causing accumulation of superoxide radicals in the cytosol and also increases their generation in mitochondria of cones. The excess superoxide radicals overwhelm superoxide dismutase 1 and 2 (SOD1 and SOD2) and cause a chain reaction by which other free radicals are generated including some that are even more damaging than superoxide radicals, such as hydroxyl radicals and peroxynitrite. The free radicals attack proteins, lipids, and DNA causing specific modifications that indicate that oxidative damage has occurred. Oxidative damage to lipids results in lipid hydroperoxides that break down to form 4-hydroxynonenal, malondialdehyde (MDA), and acrolein. The most common modification to proteins from oxidative damage is the formation of carbonyl adducts. Measurements of these markers of oxidative damage, such as MDA or the carbonyl adducts, provide a quantitative assessment of the amount of oxidative damage that has occurred in a tissue. These modifications can impair the function of macromolecules and while there are endogenous repair processes, they are overwhelmed by sever oxidative stress resulting in reduced cellular function and eventually apoptosis. After rods are eliminated from the photoreceptor layer, oxidative stress in the outer retina is severe and leads to gradual cone cell death usually starting in the midperiphery where cone density is low and then spreading peripherally and posteriorly. The posterior spread of cone death results in constriction of the visual field and eventually a central island of vision and its elimination causes blindness.

Clinical signs of RP include pigmentary changes in the retina, often around blood vessels and characterized as "bone spicule-like pigmentation", constriction of retinal vessels, and optic disc pallor. Spectral domain optical coherence tomography can show thinning of the retina in areas of photoreceptor cell loss and with segmentation the loss is seen in the outer nuclear layer. Visual field testing shows constriction of the visual fields and electroretinograms show reduced a- and b-wave amplitudes.

Currently, there is no approved therapy that stops the evolution of the disease or restores vision. The therapeutic approach is restricted to slowing down the degenerative process by sunlight protection and vitamin A supplementation, treating complications (cataract and macular edema), and helping patients to cope with the social and psychological impact of blindness. Although the Argis II Retinal Prosthesis System was approved by FDA in 2013 as an implanted device to treat adults with several RP, it only produces the sensation of light, thereby helping patients identify the location or movement of objects and people; the device is not disease modifying. Based on studies in animal models described below, NACA is able to treat RP in vivo.

The present inventors had previously found that N-acetylcysteine (NAC), a well-known thiol antioxidant, reduces cone cell death and preserves cone function in models of RP. N-acetyl-L-cysteine (NAC) is a well-known thiol-containing antioxidant that has been approved by FDA as an antidote for acetaminophen intoxication and has been used in the clinic for over 50 years for indications including mucolytic therapy for respiratory conditions with excessive and/or thick mucus production, prevention of radiocontrast-induced nephrotoxicity, treatment of cyclophosphamide-induced hemorrhagic cystitis, and reduction of symptoms of both schizophrenia and bipolar disease. NAC's effectiveness has been primarily attributed to its ability to reduce extracellular cysteine to cysteine and as a source of sulfhydryl groups. However, use of NAC has been limited by several drawbacks, most importantly low membrane penetration and <10% systemic bioavailability for oral formulations. Disulfide linkage to proteins and deacetylation of NAC in the intestinal mucosa and lumen are probably the greatest factors in the low oral bioavailability of NAC.

As such, there still exists a need for novel compositions and methods for treatment of retinitis pigmentosa.

SUMMARY

As embodied and broadly described herein, an aspect of the present disclosure relates to a method for the treatment of retinitis pigmentosa in a human comprising administering to the human a therapeutically effective amount of a composition comprising N-acetylcysteine amide (NACA) to treat the retinitis pigmentosa, wherein the NACA is administered in a therapeutically effective amount of a solid dose of N-acetylcysteine amide (NACA) at 0.5, 1, 2, 3, 3.6, 4, 5, 6, 7, 7.14, 7.2, 8, 9, 10, 15, 20, 25, 30, 40, 50, 60, 75, 80, 90, 100, 110, 120, 125, 130, 140, 150, 160, 170, 175, 180, 190, 200, 210, 220, or 225 mg/Kg, wherein NACA has more than a 2-fold greater effect on cone cell function and cone survival in retinitis pigmentosa than NAC at the same dose, wherein the therapeutically effective amount refers to the amount of a therapeutic agent that decreases at least one of the loss of night vision, the loss of overall visual acuity, the loss of visual field, by at least 10%, at least 15%, at least 20%, at least 25%, at least 30%, at least 35%, at least 40%, at least 45%, at least 50%, at least 55%, at 30 least 60%, at least 65%, at least 70%, at least 75%, at least 80%, at least 85%, at least 90%, at least 95%, or more as compared to an untreated control subject over a defined period of time, selected from at least one of 2 weeks, one month, 2 months, 3 months, 6 months, one year, 2 years, or 5 years. In one aspect, the NACA is provided in or with a pharmaceutically acceptable carrier. In another aspect, the NACA is administered intraocularly, subretinally, intravitreally, orally, intravenously, intramuscularly, intramedullarly, intrathecally, intraventricularly, transdermally, subcutaneously, intraperitoneally, intranasally, enterally, topically, sublingually, or rectally. In another aspect, the NACA is administered in daily doses of about 0.5, 1, 2, 3, 3.6, 4, 5, 6, 7, 7.14, 7.2, 8, 9, 10, 15, 20, 25, 30, 40, 50, 60, 75, 80, 90, 100, 110, 120, 125, 130, 140, 150, 160, 170, 175, 180, 190, 200, 210, 220, or 225 mg/Kg. In another aspect, the NACA is administered two or three times daily. In another aspect, the dose for administration is 50, 100, 150, 150, 300, 333, 400, 500, 600, 700, 750 mg per dose. In another aspect, the NACA is delivered orally via a mini-tablet, capsule, tablet, effervescent, dual release, mixed release, sachet, powder, or liquid.

As embodied and broadly described herein, an aspect of the present disclosure relates to a method for the treatment of retinitis pigmentosa comprising: identifying a human in need of treatment for retinitis pigmentosa; and administering to the human a therapeutically effective amount of a composition comprising N-acetylcysteine amide (NACA) to treat the retinitis pigmentosa, wherein the NACA is administered in a therapeutically effective amount of a solid dose of N-acetylcysteine amide (NACA) at 0.5, 1, 2, 3, 3.6, 4, 5, 6, 7, 7.14, 7.2, 8, 9, 10, 15, 20, 25, 30, 40, 50, 60, 75, 80, 90, 100, 110, 120, 125, 130, 140, 150, 160, 170, 175, 180, 190, 200, 210, 220, or 225 mg/Kg, wherein NACA has more than a 2-fold greater effect on cone cell function and cone survival in retinitis pigmentosa than NAC at the same dose, wherein the therapeutically effective amount refers to the amount of a therapeutic agent that decreases at least one of the loss of night vision, the loss of overall visual acuity, the loss of visual field, by at least 10%, at least 15%, at least 20%, at least 25%, at least 30%, at least 35%, at least 40%, at least 45%, at least 50%, at least 55%, at 30 least 60%, at least 65%, at least 70%, at least 75%, at least 80%, at least 85%, at least 90%, at least 95%, or more as compared to an untreated control subject over a defined period of time, selected from at least one of 2 weeks, one month, 2 months, 3 months, 6 months, one year, 2 years, or 5 years. In one aspect, the NACA is provided in or with a pharmaceutically acceptable carrier. In another aspect, the NACA is administered intraocularly, subretinally, intravitreally, orally, intravenously, intramuscularly, intramedullary, intrathecally, intraventricularly, transdermally, subcutaneously, intraperitoneally, intranasally, enterally, topically, sublingually, or rectally. In another aspect, the NACA is administered in daily doses of about 0.5, 1, 2, 3, 3.6, 4, 5, 6, 7, 7.14, 7.2, 8, 9, 10, 15, 20, 25, 30, 40, 50, 60, 75, 80, 90, 100, 110, 120, 125, 130, 140, 150, 160, 170, 175, 180, 190, or 200 mg/Kg. In another aspect, the NACA is administered two or three times daily. In another aspect, the dose for administration is 100, 150, 150, 300, 333, 400, 500, 600, 700, 750 mg per dose. In another aspect, the NACA is delivered orally via a mini-tablet, capsule, tablet, effervescent, dual release, mixed release, sachet, powder, or liquid.

As embodied and broadly described herein, an aspect of the present disclosure relates to a method for treating an eye disease caused by oxidative damage in an animal or human in need thereof, the method comprising: identifying that the subject has retinitis pigmentosa associated with Usher syndrome (RP/USH); and providing an effective amount of an N-acetylcysteine amide (NACA) sufficient to inhibit degradation of an Ellipsoid Zone (EZ) area. In one aspect, the eye disease is retinitis pigmentosa associated with Usher syndrome (RP/USH). In another aspect, the NACA is provided orally, peritoncally, intravenously, dermally, bucally, sublingually, topically, topical ocularly, intraocularly, intravitreally, transmucosally, or by inhalation. In another aspect, the NACA inhibits the reduction in EZ area measured by Spectral-Domain-Optical Coherence Tomography (SD-OCT). In another aspect, the NACA is dosed as multiple tablets per day. In another aspect, the NACA is dosed greater than 200 mg per day. In another aspect, the NACA is dosed at 500 mg per day. In another aspect, the NACA is dosed for at least 6 months, 9 months, 12 months, 18 months or 24 months. In another aspect, the NACA is dosed for less than 6 months. In another aspect, the NACA is dosed for at least one of 6, 9, 12, 18, or 24 months. In another aspect, the NACA is dosed for more than 24 months. In another aspect, the NACA is administered in daily doses of about 0.5, 1, 2, 3, 3.6, 4, 5, 6, 7, 7.14, 7.2, 8, 9, 10, 15, 20, 25, 30, 40, 50, 60, 75, 80, 90, 100, 110, 120, 125, 130, 140, 150, 160, 170, 175, 180, 190, 200, 210, 220, or 225 mg/Kg.

In accordance with an embodiment, the present invention provides a method for the treatment of retinitis pigmentosa in an animal that comprises administering to the animal a therapeutically effective amount of N-acetylcystein amide (NACA). In one aspect, the NACA is provided in or with a pharmaceutically acceptable carrier. In another aspect, the NACA is administered intraocularly, subretinally, intravitreally, orally, intravenously, intramuscularly, intramedullarily, intrathecally, intraventricularly, transdermaly, subcutaneously, intraperitoneally, intranasally, enterally, topically, sublingually, or rectally. In another aspect, the NACA is administered in daily doses of about 0.5, 1, 2, 3, 3.6, 4, 5, 6, 7, 7.14, 7.2, 8, 9, 10, 15, 20, 25, 30, 40, 50, 60, 75, 80, 90, 100, 110, 120, 125, 130, 140, 150, 160, 170, 175, 180, 190, 200, 210, 220, or 225 mg/Kg. In another aspect, NACE is administered two or three times daily. In another aspect, NACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytouene (BHT), lecithin, propyl gallate, α-tocopherol, citric acid, ethylenediamine tetraacetic acid (EDTA), sorbitol, tartaric acid, or phosphoric acid. In another aspect, the dose for administration is 10, 15, 20, 25, 30, 40, 50, 60, 75, 80, 90, 100, 150, 150, 300, 333, 400, 500, 600, 700, 750, 800, 900, 1,000, 2,500, 5,000, 7,500, or 10,000 mg per dose. In another aspect, the does for administration is 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA is delivered orally via a mini-tablet, capsule, tablet, effervescent, dual release, mixed release, sachet, powder, or liquid. In another aspect, the NACA is administered prophylactically to prevent retinitis pigmentosa. In another aspect, the animal is a human.

In accordance with another embodiment, the present invention includes a method for the treatment of retinitis pigmentosa comprising: identifying a human in need of treatment for retinitis pigmentosa; and administering to the human a therapeutically effective amount of N-acetylcysteine amide (NACA) sufficient to treat retinitis pigmentosa. In one aspect, the NACA is provided in or with a pharmaceutically acceptable carrier. In another aspect, the NACA is administered intraocularly, subretinally, intravitreally, orally, intravenously, intramuscularly, intramedullarily, intrathecally, intraventricularly, transdermaly, subcutaneously, intraperitoneally, intranasally, enterally, topically, sublingually, or rectally. In another aspect, the NACA is administered in daily doses of about 0.5, 1, 2, 3, 3.6, 4, 5, 6, 7, 7.14, 7.2, 8, 9, 10, 15, 20, 25, 30, 40, 50, 60, 75, 80, 90, 100, 110, 120, 125, 130, 140, 150, 160, 170, 175, 180, 190, 200, 210, 220, or 225 mg/Kg. In another aspect, NACE is administered two or three times daily. In another aspect, NACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytouene (BHT), lecithin, propyl gallate, α-tocopherol, citric acid, ethylenediamine tetraacetic acid (EDTA), sorbitol, tartaric acid, or phosphoric acid. In another aspect, the dose for administration is 10, 15, 20, 25, 30, 40, 50, 60, 75, 80, 90, 100, 150, 150, 300, 333, 400, 500, 600, 700, 750, 800, 900, 1,000, 2,500, 5,000, 7,500, or 10,000 mg per dose. In another aspect, the dose for administration is 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA is delivered orally via a minitablet, capsule, tablet, effervescent, dual release, mixed release, sachet, powder, or liquid. In another aspect, the NACA is administered prophylactically to prevent retinitis pigmentosa.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION

Figures 1A, 1B, 1C, 1D, 1E:
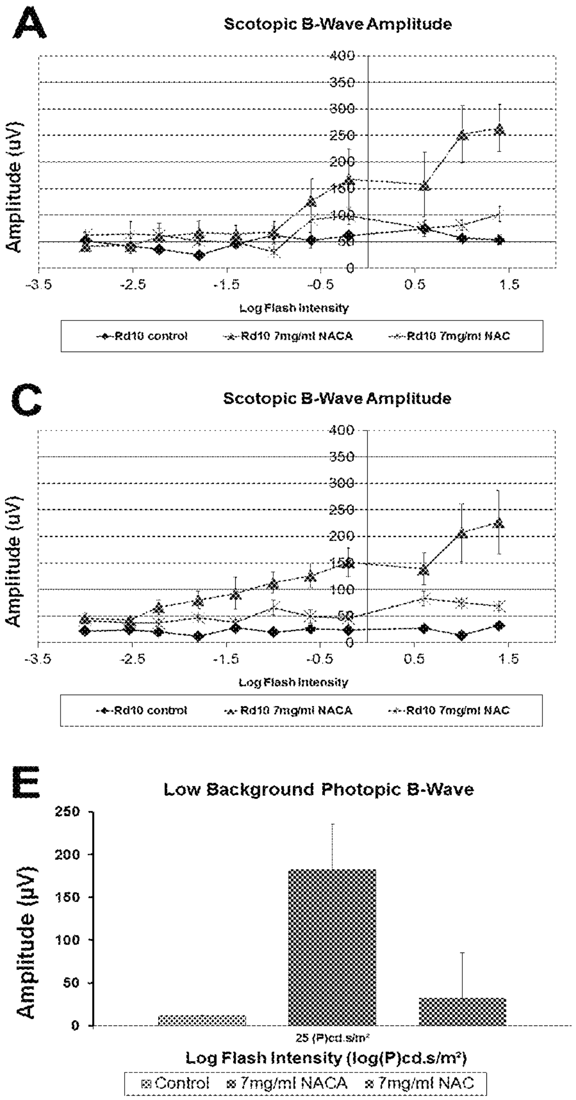
FIGS. 1A to 1E are graphs that show that 7 mg/ml NACA provides better effects than 7 mg/ml NAC in protecting retinal function.

While the making and using of various aspects of the present disclosure are discussed in detail below, it should be appreciated that the present disclosure provides many applicable inventive concepts that can be embodied in a wide variety of specific contexts. The specific aspects discussed herein are merely illustrative of specific ways to make and use the disclosure and do not delimit the scope of the disclosure.

To facilitate the understanding of this disclosure, a number of terms are defined below. Terms defined herein have meanings as commonly understood by a person of ordinary skill in the areas relevant to the present disclosure. Terms such as "a", "an" and "the" are not intended to refer to only a singular entity, but include the general class of which a specific example may be used for illustration. The terminology herein is used to describe specific aspects of the disclosure, but their usage does not delimit the disclosure, except as outlined in the claims.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Retinitis pigmentosa ("RP") comprises a large group of inherited vision disorders that cause progressive loss of photoreceptor cells of the retina, leading to severe vision impairment and often incurable blindness. The most common form of RP is a rod-cone dystrophy, in which the first symptom is night blindness, followed by progressive loss in the peripheral visual field in daylight, and eventually leading to blindness after several decades. As a common pathology, rod photoreceptors die early, whereas light-insensitive, morphologically altered cone photoreceptors persist longer.

N-acetyl-L-cysteine amide (NACA), also known as (R)-2-(acetylamino)-3-mercapto-propanamide, N-acetyl-L-cysteinamide, or acetylcysteinamide, has the structure:

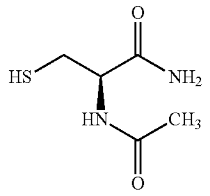

N-acetylcysteine amide (NACA), the amide form of N-acetyl-L-cysteine (NAC), acts as a carrier of NAC.

Currently, there is no approved therapy that stops the evolution of the disease or restores vision. The therapeutic approach is restricted to slowing down the degenerative process by sunlight protection and vitamin A supplementation, treating complications (cataracts and macular edema), and helping patients to cope with the social and psychological impact of blindness. Although the Argis II Retinal Prosthesis System was approved by FDA in 2013 as an implanted device to treat adults with severe RP, it only produces the sensation of light, thereby helping patients identify the location or movement of objects and people; the devise is not disease modifying. Based on studies in animal models described below, NACA is able to treat RP in vivo.

Gluthathione (GSH) is a tripeptide, c-L-glutamyl-L-cysteinyl-glycine, found in all mammalian tissues. It has several important functions including detoxification of electrophiles, scavenging ROS< maintaining the thiol status of proteins, and regeneration of the reduced forms of vitamins C and E. GSH is the dominant non-protein thiol in mammalian cells; as such it is essential in maintaining the intracellular redox balance and the essential thiol status of proteins. Also, it is necessary for the function of some antioxidant enzymes such as the glutathione peroxidases.

Intracellular GSH levels are determined by the balance between production and loss. Production results from de novo synthesis and regeneration of GSH from GSSG by GSSG reductase. Generally there is sufficient capacity in the GSSG reductase system to maintain all intracellular GSH in the reduced state, so little can be gained by ramping up that pathway. The major source of loss of intracellular GSH is transport out of cells. Intracellular GSH levels range from 1-8 mM while extracellular levels are only a few μM; this large concentration gradient essentially precludes transport of GSH into cells and once it is transported out of cells, it is rapidly degraded by γ-glutamyltranspeptidase. Inhibition of GSH transporters could theoretically increase intracellular GSH levels, but is potentially problematic because the transporters are not specific for GSH and their suppression could lead imbalance of other amino acids and peptides. Thus, intracellular GSH levels are modulated primarily by changes in synthesis.

GSH is synthesized in the cytosol of virtually all cells by two ATP-requiring enzymatic steps: L-glutamate+L-cysteine+ATP [→] γ-glutamyl-L-cysteine+ADP+Pi and γ-glutamyl-L-cysteine+L-glycine+ATP [→] GSH+ADP+Pi. The first reaction is rate-limiting and is catalyzed by glutamate cysteine ligase (GCL, EC 6.3.2.2). GCL is composed of a 73 Kd heavy catalytic subunit (GCLC) and a 30 Kd modifier subunit (GCLM), which are encoded by different genes. GCCL is regulated by nonallosteric competitive inhibition of GSH (Ki=2.3 mM) and by the availability of L-cysteine. The apparent Km of GLC for glutamate is 1.8 mM and intracellular glutamate concentration is roughly 10-fold higher so that glutamate is not limiting, but the Km for cysteine is 0.1-0.3 mM, which approximates its intracellular concentration. The second reaction is catalyzed by GSH synthase (GS, EC 6.3.2.3), which is 118 Kd and composed of two identical subunits. While GS is not felt to be important in regulation of GSH synthesis under normal conditions, it may play a role under stressful conditions because in response to surgical trauma, GSH levels and GS activity were reduced while GCL activity was unchanged. Furthermore, compared to increased expression of GCLC alone, increased expression of both GCLC and GS resulted in higher levels of GSH. In order to maximize the effects of increasing synthetic enzymes, it is necessary to provide increased levels of cysteine. In cultured neurons, 90% of cysteine uptake occurs through by the sodium-dependent excitatory amino acid transporter (EAAT) system. There are five EAATs and cysteine uptake by neurons occurs predominantly by EAAT3 more commonly known as excitatory amino acid carrier-1 (EAAC1). Under normal circumstances most EAAC1 is in the ER and only translocates to the plasma membrane when activated. This translocation is negatively regulated by glutamate transporter associated protein 3-18 (GTRAP3-18) and suppression of GTRAP3-18) increased GSH levels in neurons. Thus, internalization of cysteine provides a road block for GSH synthesis, but fortunately it can be bypassed by N-acetylcysteine (NAC) which readily enters cells even in the absence of activated EAAC1. Systemically administered NAC gains access to the CNS, increases GSH levels, and provides benefit in neurodegenerative disorders in which oxidative stress is an important part of the pathogenesis. The present inventors have demonstrated that orally administered NAC promotes long term survival of cones in a model of RP.

All cellular compartments must be protected against oxidative damage, including the cytoplasm, mitochondria and the nucleus. The present inventors have previously performed gene transfer of enzymes that detoxify reactive oxygen species, but that approach requires expression of two enzymes in the cytoplasm and two enzymes in mitochondria. In contrast, the present invention provides for protection of all cellular compartments with expression of only two enzymes in the cytosol because GSH is able to diffuse everywhere throughout cells.

NAC is used for the treatment of acetaminophen overdose at a dose of 140 mg/kg as the loading dose, followed by 70 mg/kg every 4 hours for 17 doses, starting 4 hours after the loading dose. In clinical studies, NAC has been administered orally from 400 to 1000 mg once daily and from 200 to 600 mg three times daily. However, following an oral dose of 600 mg in humans, NAC is rapidly absorbed and then rapidly cleared. The plasma half-life of NAC has been reported to be 2.5 hours and no NAC is detectable 10-12 hours after administration. During absorption, NAC is rapidly metabolized to cysteine, which is a direct precursor of glutathione. Based on this evidence, including that NACA is a precursor and/or carrier for NAC, it was expected that NACA would act similarly to NAC in vivo. However, the present inventors demonstrate that NACA acts very differently from NAC for the treatment of RP.

In accordance with an embodiment, the present invention provides a method for the prevention, amelioration, or treatment of a disease or condition associated with oxidative stress in a subject comprising administration of a therapeutically effective amount of NACA, to increase the amount of glutathione expressed in the tissues of the subject.

As used herein, "active oxygen species" or "reactive oxygen species" are understood as transfer of one or two electrons produces superoxide, an anion with the form O2", or peroxide anions, having the formula O22-" or compounds containing an O—O single bond, for example hydrogen peroxides and lipid peroxides. Such superoxides and peroxides are highly reactive and can cause damage to cellular components including proteins, nucleic acids, and lipids.

An "agent" is understood herein to include a therapeutically active compounds or a potentially therapeutic active compound, e.g., an antioxidant. An agent can be a previously known or unknown compound. As used herein, an agent is typically a non-cell based compound, however, an agent can include a biological therapeutic agent, e.g., peptide or nucleic acid therapeutic, e.g., siRNA, shRNA, cytokine, antibody, etc.

As used herein "amelioration" or "treatment" is understood as meaning to lessen or decrease at least one sign, symptom, indication, or effect of a specific disease or condition. For example, amelioration or treatment of retinitis pigmentosa (RP) can be to reduce, delay, or eliminate one or more signs or symptoms of RP including, but not limited to, a reduction in night vision, a reduction in overall visual acuity, a reduction in visual field, a reduction in the cone density in one or more quadrants of the retina, thinning of retina, particularly the outer nuclear layer, reduction in a- or b-wave amplitudes on scotopic or photopic electroretinograms (ERGs); or any other clinically acceptable indicators of disease state or progression. Amelioration and treatment can require the administration of more than one dose of an agent, either alone or in conduction with other therapeutic agents and interventions. Amelioration or treatment does not require that the disease or condition be cured.

"Antioxidant" as used herein is understood as a molecule of slowing or preventing the oxidation of other molecules. Oxidation is a chemical reaction that transfers electrons from a substance to an oxidizing agent. Such reactions can be promoted by or produce superoxide anions or peroxides. Oxidation reactions can produce free radicals, which start chain reaction that damage cells. Antioxidants terminate these chain reactions by removing free radical intermediates, and inhibit other oxidation reactions by being oxidized themselves. As a result, antioxidants are often reducing agents such as thiols, ascorbic acid or polyphenols. Antioxidants include, but are not limited to, α-tocopherol, ascorbic acid, Mn(III) tetrakis(4-benzoic acid) porphyrin, α-lipoic acid, and n-acetylcysteine.

"Co-administration" as used herein is understood as administration of one or more agents to a subject such that the agents are present and active in the subject at the same time. Co-administration does not require a preparation of an admixture of the agents or simultaneous administration of the agents.

The terms "effective amount" or "effective doses" refers to that amount of an agent to product the intended pharmacological, therapeutic or preventive results. The pharmacologically effective amount results in the amelioration of one or more signs or symptoms of a disease or condition or the advancement of a disease or conditions, or causes the regression of the disease or condition. For example, a therapeutically effective amount preferably refers to the amount of a therapeutic agent that decreases the loss of night vision, the loss of overall visual acuity, the loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, e.g., 2 weeks, one month, 2 months, 3 months, 6 months, one year, 2 years, 5 years, or longer. More than one dose may be required to provide an effective dose.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such as treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as an improvement of symptoms, a cure, a reduction in disease signs or symptoms, extension of life, improvement in quality of life, or other effect generally recognized as positive by medical doctors familiar with treating the particular type of disease or condition.

"Oxydative stress related ocular disorders" as used herein include, but are not limited to, retinitis pigmentosa, macular degeneration including age related macular degeneration (AMD) both wet and dry, diabetic retinopathy, Lebers optic neuropathy, and optic neuritis.

"Peroxidases" or "a peroxide metabolizing enzyme" are a large family of enzymes that typically catalyze a reaction of the form:

$$ROOR^1 + \text{electron donor (2 e-)} + 2H + \longrightarrow ROH + R^1OH$$

For many of these enzymes the optimal substrate is hydrogen peroxide, wherein each R is H, but others are more active with organic hydroperoxides such as lipid peroxides. Peroxidases can contain a heme cofactor in their active sites, or redox-active cysteine or selenocysteine residues.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations, particularly phosphate buffered saline solutions which are preferred for intraocular delivery.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, intraocular, intravitreal, subretinal, and/or other routes of parenteral administration. The specific route of administration will depend, inter alia, on the specific cell to be targeted. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

As used herein, "prevention" is understood as to limit, reduce the rate or degree of onset, or inhibit the development of at least one sign or symptom of a disease or condition particularly in a subject prone to developing the disease or disorder. For example, a subject having a mutation in a gene, such as the opsin gene, is likely to develop RP. The age of onset of one or more symptoms of the disease can sometimes be determined by the specific mutation. Prevention can include the delay of onset of one or more signs or symptoms of RP and need not be prevention of appearance of at least one sign or symptom of the disease throughout the lifetime of the subject. Prevention can require the administration of more than one does of an agent or therapeutic.

"Small molecule" as used herein is understood as a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

A "subject" as used herein refers to living organisms. In certain embodiments, the living organism is an animal, in certain preferred embodiments, the subject is a mammal, in certain embodiments, the subject is a domesticated mammal or a primate including a non-human primate. Examples of subject include humans, monkeys, dogs, cats, mice, rates, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition or syndrome. Methods for identification of subjects suffering from or suspected of suffering from conditions such as RP and age-related macular degeneration (AMD) is within the ability of those in the art. Subjects suffering from, and suspected of suffering from, a specific disease, condition, or syndrome are not necessarily two distinct groups.

As used herein, "superoxide dismutase" is understood as an enzyme that dismutation of superoxide into oxygen and hydrogen peroxide. Examples include, but are not limited to SOD1, SOD2, and SOD3. Sod1 and SOD3 are two isoforms of Cu—Zn-containing superoxide dismutase enzymes exists in mammals. Cu—Zn-SOD or SOD1, is found in the intracellular space, and extracellular SOD (ECSOD or SOD3) predominantly is found in the extracellular matrix of most tissues.

"Therapeutically effective amount," as used herein refers to an amount of an agent which is effective, upon single or multiple does administration to the cell or subject, in prolonging the survivability of the patient with such a disorder, reducing one or more signs or symptoms of the disorder, preventing or delaying and the like beyond that expected in the absence of such treatment.

An agent or other therapeutic intervention can be administered to a subject, either alone or in combination with one or more additional therapeutic agents or interventions, as a pharmaceutical composition in mixture with conventional excipient, e.g., pharmaceutically acceptable carrier, or therapeutic treatments.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, PA, 1985). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

The present invention is directed to the use of NACA to treat RP. In one embodiment, the present invention includes a method for the treatment of retinitis pigmentosa in a human that comprises administering to the human therapeutically effective amount of NACA. In some embodiments, the NACA is provided in or with a pharmaceutically acceptable carrier. In other embodiments, the NACA is administered intraocularly, subretinally, intravitreally, orally, intravenously, intramuscularly, intramedullarily, intrathecally, intraventricularly, transdermaly, subcutaneously, intraperitoneally, intranasally, enterally, topically, sublingually, or rectally.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the forgoing guidelines.

Ranges provided herein are understood to be shorthand for all of the values within the range.

As used herein, the embodiments of this invention are defined to include pharmaceutically acceptable derivatives thereof. A "pharmaceutically acceptable derivative" means any pharmaceutically salt, ester, salt of an ester, or other derivative of a compound of this invention which, upon administration to a recipient, is capable of providing (directly or indirectly) a compound of this invention. Particularly favored derivatives are those that increase the bioavailability of the compounds of this invention when such compounds are administered to a mammal (e.g., by allowing an orally administered compound to be more readily absorbed into the blood, to increase serum stability or decrease clearance rate of the compound) or which enhance delivery of the parent compound to a biological compartment (e.g., the brain or lymphatic system) relative to the parent species. Derivatives include derivatives where a group which enhances aqueous solubility or active transport through the gut membrane is appended to the structure of formulae described herein.

The embodiments of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-napthalenesulfonate, nicotinate, nitrate, palmoate, phosphate, picrate, pivalate, propionate, salicylate, succinate, sulfate, tartrate, tosylate, and undeconaoate. Salts derived from appropriate bases include alkali metal (e.g., sodium), alkaline earth metal (e.g., magnesium), ammonium and N-(alkyl) 4+ salts. This invention also envisions the quaternization of any basic nitrogen-containing groups of the compounds disclosed herein. Water or oil-soluble or dispersible products may be obtained by such quaternization.

The embodiments of the invention can, for example, be administered by injection, intraocularly, intravitreally, subretinal, intravenously, intraarterially, subdermally, intraperitoneally, intramuscularly, or subcutancously; or orally, buccally, nasally, transmucosally, directly to a diseased organ by catheter, topically, or in an ophthalmic preparation, with a dosage ranging from about 0.001 to about 100 mg/kg of body weight, or according to the requirements of the particular drug and more preferably from 0.5-10 mg/kg of body weight. It is understood that when a compound is delivered directly to the eye, considerations such as body weight have less bearing on the dose.

Frequency of dosing will depend on the agent administered, the progression of the disease or condition in the subject, and other considerations known to those of skill in the art. For example, pharmacokinetic and pharmacodynamics considerations for compositions delivered to the eye, or even compartments within the eye, are different, e.g., clearance in the subretinal space is very low. Therefore, dosing can be as infrequent as once a month, once every three months, once every six months, once a year, once every five years, or less. If systemic administration of antioxidants is to be performed in conjunction with administration of expression constructs to the subretinal space, it is expected that the dosing frequency of the antioxidant will be higher than the expression construct, e.g., one or more times daily, one or more times weekly.

Dosing may be determined in conjunction with monitoring of one or more signs or symptoms of the disease, e.g., visual acuity, visual field, night visions, etc. The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity ad course of the disease, condition or symptoms, the patient's disposition to the disease, condition or symptoms and the judgment of the treating physician.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, TWEEN® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as TWEENs® or SPAN® and/or other similar emulsifying agents or bioavailability enhancers which are commonly used in the manufacture of pharmaceutically acceptable solid, liquid, or other dosage forms may also be used for the purposes of formulation.

In one or more embodiments, NACA is administered in daily doses of about 0.5 to 150 mg/Kg. In other embodiments, NACA is administered two or three times daily. In another aspect, NACA is administered with a second active agent selected from ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

In some embodiments, the dose of NACA for administration is 100, 150, 150, 300, 333, 400, 500, 600, 700, 750, 800, 900, 1,000, 2,500, 5,000, 7,500, or 10,000 mg per dose. In another aspect, the dose for administration is 0.1-0.25, 0.1-0.4, 0.35-0.5, 0.5-1, 102, 1-3, 1-4, 1-5, 1-2.5, 2.5-3.5, 4-6, 5-8, 6-9, 7-10 grams per dose. In another aspect, the NACA is delivered orally via a mini-tablet, capsule, tablet, effervescent, dual release, mixed release, sachet, powder, or liquid. In another aspect, the NACA is administered prophylactically to prevent RP.

In another embodiment, the present invention includes a method for the treatment of RP comprising: identifying a human in need of treatment for retinitis pigmentosa; and administering to the human a therapeutically effective amount of NACA sufficient to treat RP. It will be understood that, as with the other embodiments defined above, NACA is administered in daily doses of about 0.5, 1, 2, 3, 4, 5, 6, 7, 8, 9, 10, 1, 20, 25, 30, 40, 50, 60, 75, 80, 90, 100, 110, 120 125, 130, 140, 150, 160, 170, 175, 180, 190, 200, 210, 220, 225 mg/Kg. In another aspect, NACA is administered two or three times daily. In another aspect, NACA is administered with a second active agent as disclosed above.

In another aspect, the dose of NACA for administration is 100, 150, 150, 300, 333, 400, 500, 600, 700, 750, 800, 900, 1,000, 2,500, 5,000, 7,500, or 10,000 mg per dose. In another aspect, the dose for administration is 0.1-0.25, 0.1-0.4, 0.35-0.5, 0.5-1, 102, 1-3, 1-4, 1-5, 1-2.5, 2.5-3.5, 4-6, 5-8, 6-9, 7-10 grams per dose. In another aspect, the NACA is delivered orally via a mini-tablet, capsule, tablet, effervescent, dual release, mixed release, sachet, powder, or liquid. In another aspect, NACA is administered prophylactically to prevent RP.

As used herein, "susceptible to" or "prone to" or "predisposed to" a specific disease or condition or the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200% or more.

Example 1

Starting at postnatal day (P) 14, rd$10^{+/+}$ mice were given normal drinking water (n=6) or water containing 7 mg/ml NACA, or 7 mg/ml NAC, or 20 mg/ml NAC (n=8 for each group). Scotopic and photopic electroretinograms (ERGs) were recorded at P35. Scotopic, photopic and low background photopic ERGs were recorded at P50.

Cone density was measured at P50 in four 230 mm×230 mm (512×512 pixels) areas located 0.5 mm superior, temporal, inferior, and nasal to the center of the optic nerve in retinal flat mounts stained with fluorescein-labeled peanut agglutinin (PNA).

Figures 2A, 2B, 2C, 2D, 2E, 2F, 2G, 2H, 2I, 2J, 2K, 2L, 2M:
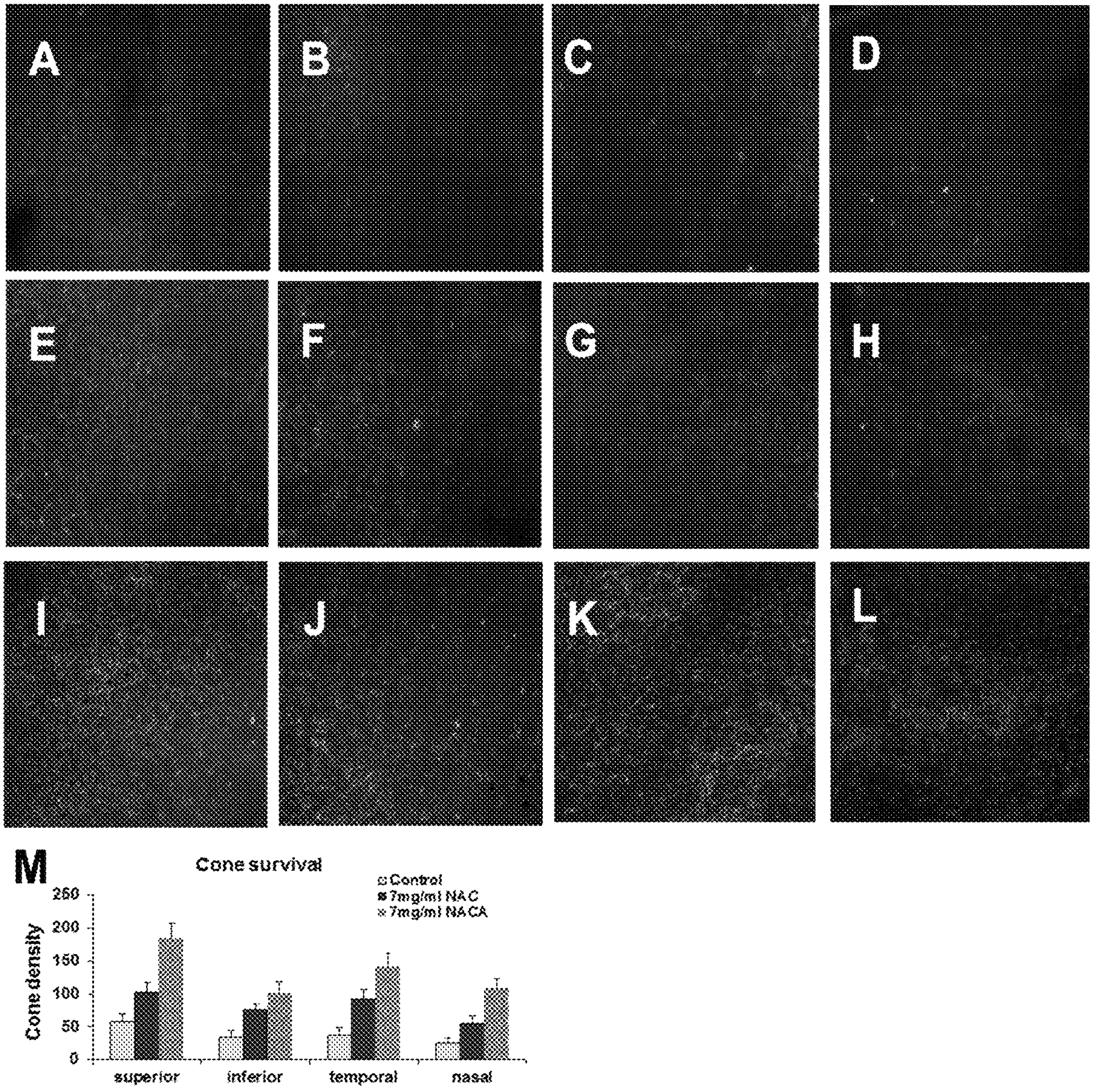
FIGS. 2A to 2L are micrographs that show that 7 mg/ml NACA provides better effects than 7 mg/ml NAC in protecting cone cell survival.
FIG. 2M is a graph that shows the cone cell survival.

It was found that, at P35, both mean peak scotopic ERG b-wave amplitude and mean5 peak photopic b-wave amplitude in rd10+/+ mice treated with 7 mg/ml NACA were more than 2-fold greater than those in rd10+/+ mice treated with 7 mg/ml NAC, and 3-fold greater than those in control rd10+/+ mice. At P50, scotopic and photopic ERG b-waves in NACA-treated mice showed 3-fold greater amplitudes than those in rd10+/+ mice treated with 7 mg/ml NAC, or control rd10+/+ mice. FIGS. 1A to 1E are graphs that show that 7 mg/ml NACA provides better effects than 7 mg/ml NAC in protecting retinal function. As shown in FIGS. 1A to 1E, the following were measured: scotopic b-wave amplitude (FIGS. 1A, IC), photopic b-wave amplitude (FIGS. 1B, 1D), and low background photopic b-wave (FIG. 1E). Cone cell density was significantly greater in 3 of 4 quadrants in NACA-treated mice compared to NAC treated mice, p<0.0001 by ANOVA with Dunnett's correction for multiple comparisons. FIGS. 2A to 2L are micrographs that show that 7 mg/ml NACA provides better effects than 7 mg/ml NAC in protecting cone cell survival. FIG. 2M is a graph that shows the cone cell survival as measured by cone density at the superior, inferior, temporal and nasal areas.

Figures 3A, 3B, 3C, 3D, 3E:
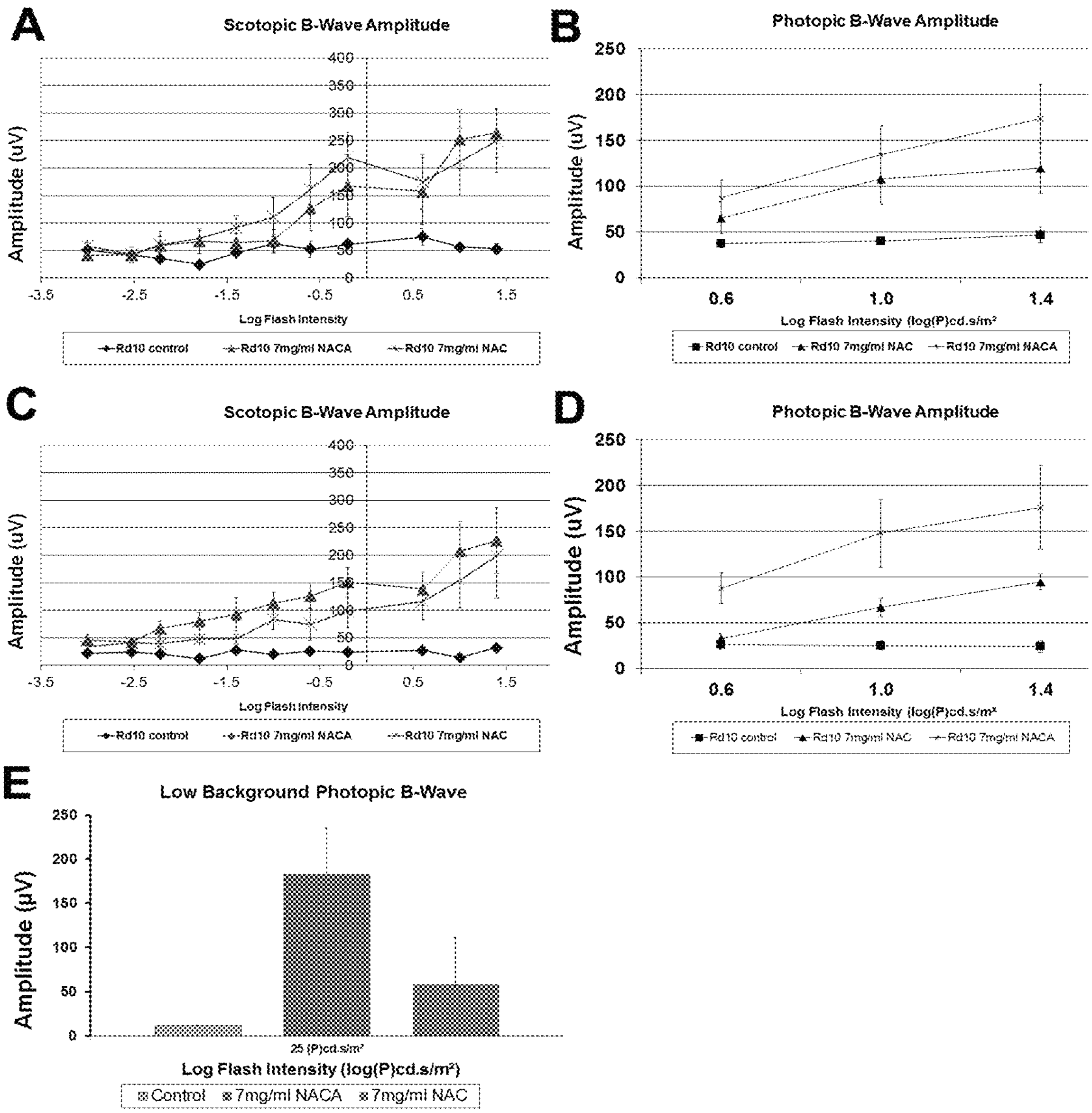
FIGS. 3A to 3E are graphs that show that 7 mg/ml NACA provides better effects than 20 mg/ml NAC in protecting retinal function.
Figures 4A, 4B, 4C, 4D, 4E, 4F, 4G, 4H, 4I, 4J, 4K, 4L, 4M:
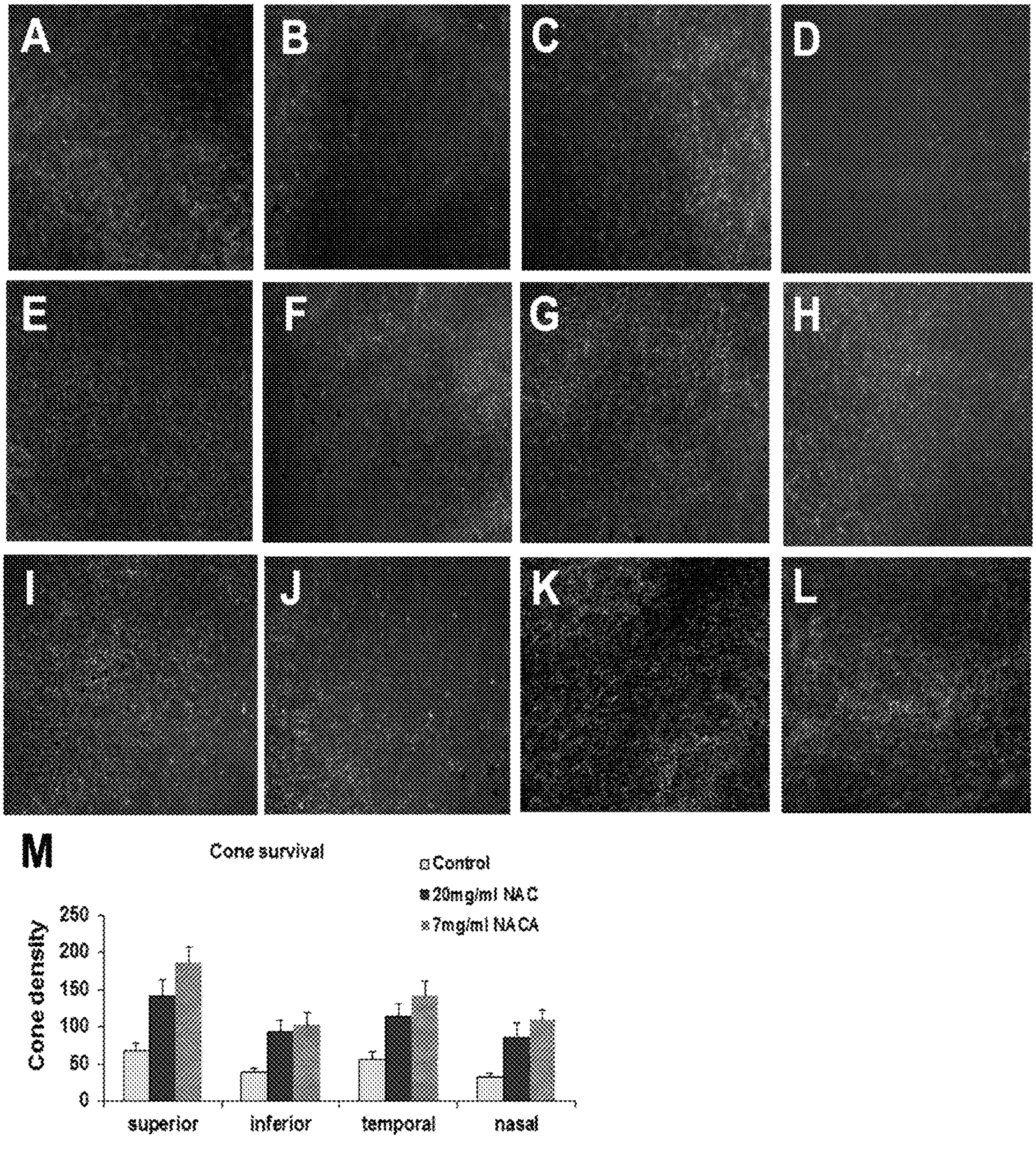
FIGS. 4A to 4L are micrographs that show that 7 mg/ml NACA has better effect than 20 mg/ml NAC in protecting cone cell survival.
FIG. 4M is a graph that shows the cone survival.

Comparing with those treated with 20 mg/ml NAC, rd10+/+ mice treated with 7 mg/ml NACA show similar mean peak scotopic ERG b-wave amplitude at P35. Mean peak photopic 20 b-wave amplitude was 41% higher (p=0.024) in NACA-treated mice than NAC-treated mice and both were more than 3-fold higher than that in controls. At P50, mean peak scotopic ERG b-wave amplitude in 20 mg/ml NAC- or 7 mg/ml NACA-treated mice showed sustained higher amplitudes than those in controls with mean b-wave amplitudes significantly greater in NACA treated mice compared with NAC-treated mice at 10 of 11 stimulus intensities. Mean photopic ERG b-wave amplitude was 50% higher (p=0.001) at all 3 stimulus intensities in NACA-treated versus NAC-treated mice and more than 4-fold greater than controls. FIGS. 3A to 3E are graphs that show that 7 mg/ml NACA provides better effects than 20 mg/ml NAC in protecting retinal function. As shown in FIGS. 3A to 3E, the following were measured: scotopic b-wave amplitude (FIGS. 3A, 3C), photopic b-wave amplitude (FIGS. 3B, 3D), and low background photopic b-wave (FIG. 3E). Cone cell density was significantly greater in 2 of 4 quadrants in NACA-treated mice compared to NAC-treated mice (FIGS. 4A to 4L). FIGS. 4A to 4L are micrographs that show that 7 mg/ml NACA has better effect than 20 mg/ml NAC in protecting cone cell survival. FIG. 4M is a graph that shows the cone survival as measured by cone density at the superior, inferior, temporal and nasal areas.

Surprisingly, at the same oral dose, or even with a substantially lower dose, NACA 5 showed significantly greater preservation of cone cell function and cone survival compared with NAC in rd10's mice. This is surprising because NACA is a precursor of NAC and it would not have been expected that the precursor would lead to a significantly different in vivo effect.

Example 2

Nacuity Pharmacetuicals, Inc., completed Clinical Study C-18-04, i.e., "Safety and Efficacy of NPI-001 Tablets versus Placebo for Treatment of Retinitis Pigmentosa Associated with Usher Syndrome (SLO RP)" (ClinicalTrials.gov Identifier: NCT04355689). The SLO RP Trial, double-masked, placebo controlled and randomized (2 active (NPI-001 tablets at 500 mg/day): 1 placebo). A treatment effect for NPI-001 Tablets was observed for Ellipsoid Zone (EZ) Area at Month 24 (change from baseline versus Pbo as determined by Spectral Domain Optical Coherence Tomography. In fact, EZ area for NPI-001 versus placebo was statistically significantly greater at 6, 9, 12, 18 and 24 month timepoints.

Figure 5:
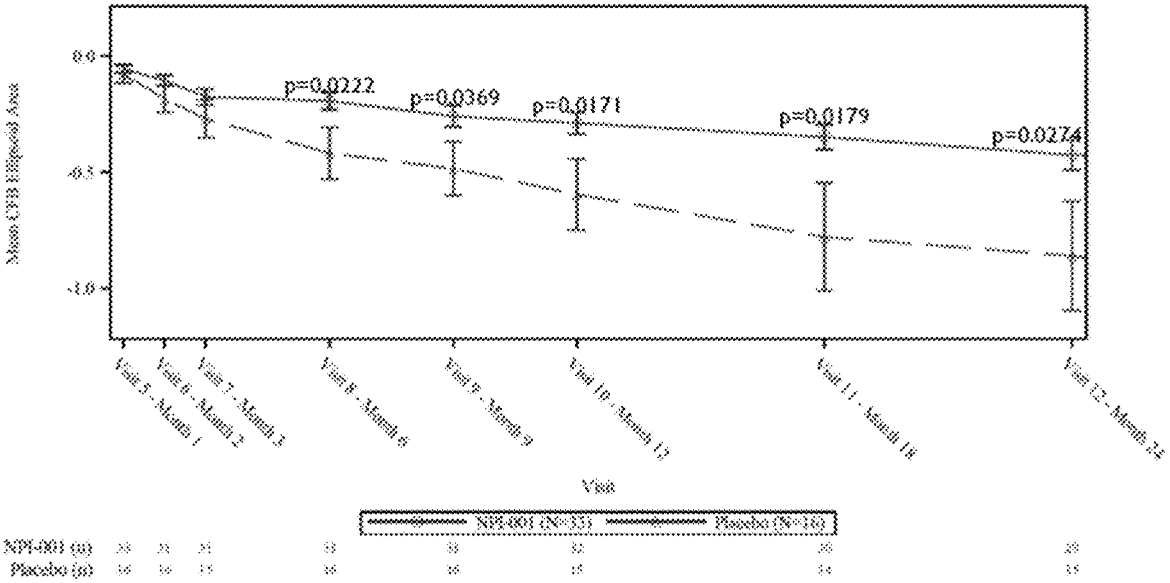
FIG. 5 shows significant slowing of photoreceptor loss with NACA (NPI-001) (solid line) versus Placebo (dashed line) by EZ area by Spectral-Domain-Optical Coherence Tomography (SD-OCT) through the 24-month visit (NCT04355689).

FIG. 5 shows significant slowing of photoreceptor loss with NACA (NPI-001) (solid line) versus Placebo (dashed line) by EZ area by Spectral-Domain-Optical Coherence Tomography (SD-OCT) through the 24-month visit (NCT04355689).

These observed effects with NPI-001 Tablets in patients with RP/USH are surprising considering the very small sample size (49 subjects) of this dataset. These observed effects with NPI-001 Tablets in patients with RP/USH are surprising because no other drug study has ever been shown to protect photoreceptor cells in patients with RP or RP/USH.

These observed effects with NPI-001 Tablets in patients with RP/USH are surprising because no other drug study has ever shown any kind of treatment effect in patients with RP or RP/USH.

It is contemplated that any aspects of the disclosure discussed in this specification can be implemented with respect to any method, kit, reagent, or composition of the disclosure, and vice versa. Furthermore, compositions of the disclosure can be used to achieve methods of the disclosure.

It will be understood that particular aspects described herein are shown by way of illustration and not as limitations of the disclosure. The principal features of this disclosure can be employed in various aspects without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In aspects of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the disclosure(s) set out in any claims that may issue from this disclosure. Specifically, and by way of example, although the headings refer to a "Field of Invention," such claims should not be limited by the language under this heading to describe the so-called technical field. Further, a description of technology in the "Background" section is not to be construed as an admission that technology is prior art to any disclosure(s) in this disclosure. Neither is the "Summary" to be considered a characterization of the disclosure(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure but should not be constrained by the headings set forth herein.

All of the compositions and/or methods disclosed and claimed herein can be made and executed without undue experimentation in light of the present disclosure. While the compositions and methods of this disclosure have been described in terms of preferred aspects, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A method for treating an eye disease caused by oxidative damage in a subject in need thereof, the method comprising:

identifying that the subject has retinitis pigmentosa associated with Usher Syndrome (RP/USH);

providing an effective amount of N-acetylcysteine amide (NACA) sufficient to slow degradation of an Ellipsoid Zone (EZ) area.

2. The method of claim 1, wherein the NACA is provided orally, peritoneally, intravenously, dermally, bucally, sublingually, topically, topical ocularly, intraocularly, intravitreally, transmucosally, or by inhalation.

3. The method of claim 1, wherein the NACA slows a reduction in the EZ area as measured by Spectral-Domain-Optical Coherence Tomography (SD-OCT).

4. The method of claim 1, wherein the NACA is dosed as single or multiple dosage units (including tablets) per day.

5. The method of claim 1, wherein the NACA is dosed at 125 mg per day.

6. The method of claim 1, wherein the NACA is dosed at 125 mg twice per day.

7. The method of claim 1, wherein the NACA is dosed at 125 mg four times per day.

8. The method of claim 1, wherein the NACA is dosed greater than 200 mg per day.

9. The method of claim 1, wherein the NACA is dosed at 250 mg per day.

10. The method of claim 1, wherein the NACA is dosed at 250 mg twice per day.

11. The method of claim 1, wherein the NACA is dosed at 500 mg per day.

12. The method of claim 1, wherein the NACA is dosed at 750 mg per day.

13. The method of claim 1, wherein the NACA is dosed at 1,000 mg per day.

14. The method of claim 1, wherein the NACA is dosed at 1,250 mg per day.

15. The method of claim 1, wherein the NACA is dosed at 1,500 mg per day.

16. The method of claim 1, wherein the NACA is dosed for at least 6 months, 9 months, 12 months, 18 months or 24 months.

17. The method of claim 1, wherein the NACA is dosed for less than 6 months.

18. The method of claim 1, wherein the NACA is dosed for at least one of 6, 9, 12, 18, or 24 months.

19. The method of claim 1, wherein the NACA is dosed for more than 24 months.

20. The method of claim 1, wherein the NACA is administered in daily doses of about 0.5, 1, 2, 3, 3.6, 4, 5, 6, 7, 7.14, 7.2, 8, 9, 10, 15, 20, 25, 30, 40, 50, 60, 75, 80, 90, 100, 110, 120, 125, 130, 140, 150, 160, 170, 175, 180, 190, 200, 210, 220, or 225 mg/Kg.

* * * * *